Jan. 13, 1953 F. W. ANDERSON Plant Pat. 1,160
NECTARINE TREE
Filed March 17, 1952
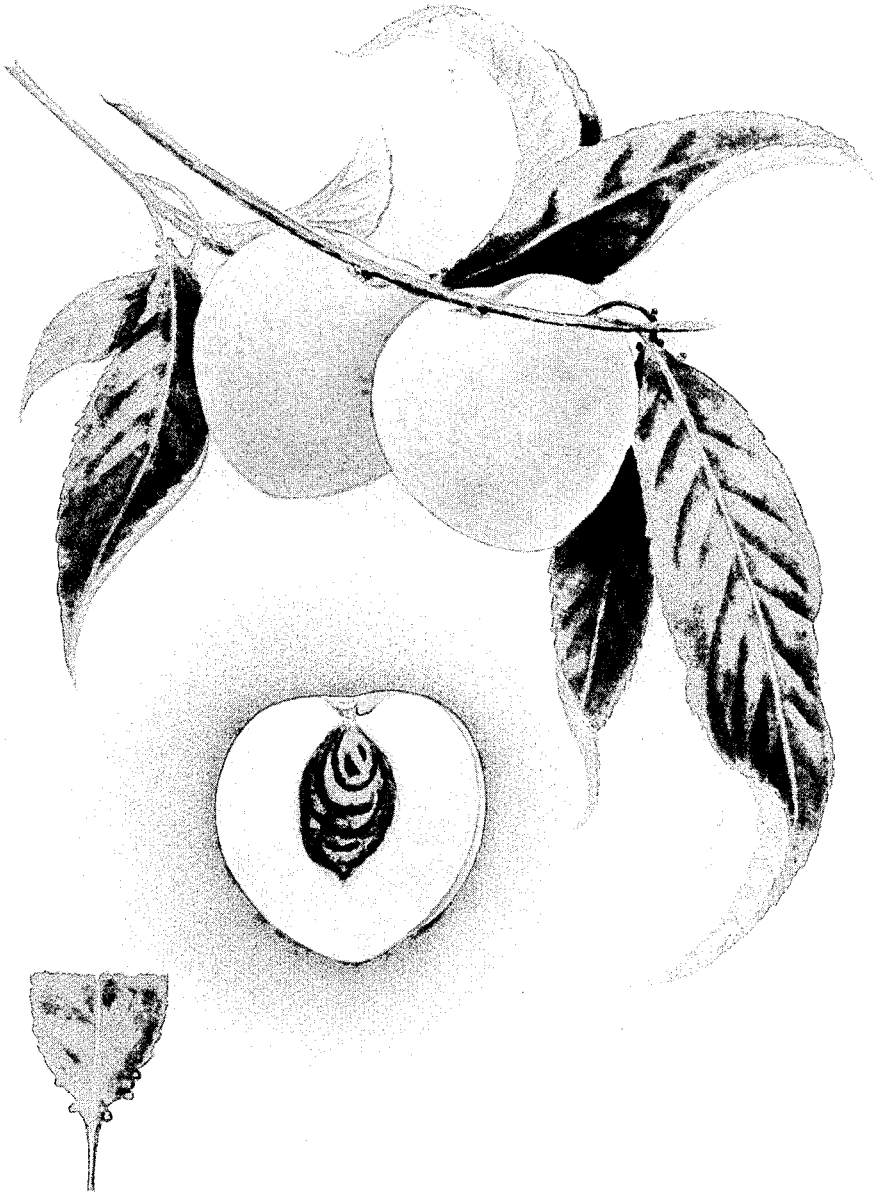
WITNESS
Addison J. Avery
INVENTOR
FREDERIC W. ANDERSON
Webster & Webster
ATTYS.

Patented Jan. 13, 1953

Plant Pat. 1,160

UNITED STATES PATENT OFFICE 1,160

NECTARINE TREE

Frederic W. Anderson, Merced, Calif., assignor to Kim Brothers, Reedley, Calif., a partnership Application March 17, 1952, Serial No. 277,031

1 Claim. (Cl. 47—62)

The present invention is directed to a new and distinct variety of nectarine tree; the primary distinguishing feature of the variety being that it provides a highly colored, yellow fleshed, freestone fruit ripening when no such comparable variety is presently available; the variety being the result of an extensive plant breeding program conducted by me in an endeavor to provide a better commercial nectarine variety, for long distance shipping, during said harvest season.

This variety of nectarine is a second generation seedling of Kim nectarine, United States Plant Patent No. 173, crossed with the July Elberta peach, United States Plant Patent No. 15.

The first generation of this cross consisted of a group of yellow-fleshed, freestone peaches, and the seeds of these—resulting from open-pollinated flowers—were planted in a nursery row and later top-worked to orchard trees. Substantially one-quarter of the resulting progeny were nectarines, and the present variety was recognized, in such group of nectarines, as being new and distinct by reason of its ripening period relative to other varieties of nectarines, as will hereinafter appear.

The origination of the variety, and its subsequent successful asexual reproduction by top-working onto orchard trees, was conducted in the experimental orchard on my ranch near Merced, county of Merced, State of California.

By careful observation I have determined that the asexual reproductions carry forward all of the distinctive characteristics of the parent tree and its fruit.

In the original drawings, on reduced scale is shown:

A perspective view of fruit of the new variety, together with stems and leaves;

A sectional view of one of the fruit, with the stone exposed; and,

A fragmentary elevation of one of the leaves, showing particularly the glands.

Referring now more specifically to the pomological details of this new and distinct variety of nectarine tree, the following is an outline description thereof; all major color plate identifications being by reference to Maerz and Paul Dictionary of Color:

Tree: Large; vigorous; spreading; open; vase formed; very productive; regular bearer.

Trunk: Medium size; medium texture.

Branches: Medium size; medium texture.

*Color.*—Brown.

*Lenticels.*—Medium size; medium number.

Leaves: Large, averaging 6″ in length and 1¾″ to 2″ in width. Medium thickness.

*Color.*—Medium green (21–L–7 to 22–L–8), lighter on under side (21–L–4).

*Margin.*—Crenate.

*Petiole.*—Medium length.

*Glands.* — Average — two. Medium length; globose mostly on blade but occasionally on petiole. No stipules.

Flower buds: Medium size; short; plump.

Flowers: Full bloom, early to medium—about with the July Elberta peach. Large size. Low chilling requirement. Color—pale pink.

Fruit: Maturity when described—hard ripe August 10, 1951.

*Size.*—Large, averaging 2¾″ in axial diameter and 2½″ transversely in the suture plane.

*Form.*—Uniform; symmetrical; oblong.

*Suture.*—A distinct line extending from base to beyond apex.

*Ventral surface.*—Rounded slightly; lips equal.

*Cavity.*—Rounded.

*Apex.*—Short.

*Skin.*—Thick; tough; no pubescence.

*Tendency to crack.*—None.

*Color.*—Yellow (11–L–6), almost completely overspread with red (3–L–11), with slight mottling or streaking.

Flesh:

*Surface of pit cavity.*—Tinged with pinkish red.

*Juice.*—Moderate.

*Texture.*—Firm; meaty.

*Fibers.*—Few.

*Ripens.*—Evenly.

*Flavor.*—Vinous.

*Aroma.*—Distinct.

*Color.*—Yellow (9–K–7).

Stone: Free; parts from flesh smoothly.

*Fibers.*—Short.

*Size.*—Medium. Average length, 1½″; average breadth, $1\frac{1}{16}$″; average thickness, ½″.

*Form.*—Oval.

*Base.*—Oblique.

*Hilum.*—Oval.

*Apex.*—Round.

*Size.*—Equal.

*Color.*—Brown (7–A–12).

Keeping quality: Very good.

Resistance to diseases: Average; controlled by conventional commercial spray practices.

Use: Dessert; long distance shipment.

In 1951 the dates of first and last picking of the fruit of the herein claimed variety were August 5th and August 15th, respectively. The present variety is thus in harvest approximately ten days later than the July Elberta peach and one month later than the freestone Sun Grand nectarine (United States Plant Patent No. 974). The Sun Grand nectarine and the present variety have the same ancestry and bear close resemblance in general characteristics, with the exception of the time of ripening.

As compared to the ripening period of other nectarine varieties, the present variety ripens immediately following the clingstone nectarine Le Grand (United States Plant Patent No. 549), and substantially with or a few days earlier than the Stanwick nectarine (not patented).

Instead of bearing fruit having soft white flesh with light skin color, as in the Stanwick, the fruit of the instant variety has firm yellow flesh with highly colored skin; the latter being yellow, almost completely overspread with red, as heretofore described.

The tree and its fruit herein described may vary in slight detail due to climatic and soil conditions under which the variety may be grown.

Having thus described my invention, I claim:

A new and distinct variety of nectarine tree substantially as described and illustrated, bearing large, firm, yellow fleshed freestone fruit yellow in color but almost completely overspread with red; such fruit ripening approximately one month later than the Sun Grand nectarine, immediately subsequent to the clingstone Le Grand nectarine, and substantially with or a few days earlier than the Stanwick nectarine.

FREDERIC W. ANDERSON.

No references cited.